(12) United States Patent
LaConte et al.

(10) Patent No.: US 10,485,577 B2
(45) Date of Patent: Nov. 26, 2019

(54) SURGICAL DEVICE WITH TRIGGERED PROPULSION SYSTEM FOR INSERTING A TROCAR-CANNULA ASSEMBLY

(71) Applicant: Synergetics USA, Inc., O'Fallon, MO (US)

(72) Inventors: Matthew Paul LaConte, Chesterfield, MO (US); James C. Easley, Cottleville, MO (US); Jason Stroisch, Wentzville, MO (US)

(73) Assignee: Synergetics USA, Inc., O'Fallon, MO (US)

( * ) Notice: Subject to any disclaimer, the term of this patent is extended or adjusted under 35 U.S.C. 154(b) by 327 days.

(21) Appl. No.: 15/047,404

(22) Filed: Feb. 18, 2016

(65) Prior Publication Data
US 2017/0238961 A1   Aug. 24, 2017

(51) Int. Cl.
*A61B 17/34*   (2006.01)
*A61F 9/007*   (2006.01)
*A61B 17/00*   (2006.01)
*A61B 90/00*   (2016.01)

(52) U.S. Cl.
CPC .......... *A61B 17/3403* (2013.01); *A61F 9/007* (2013.01); *A61B 17/3462* (2013.01); *A61B 2017/00398* (2013.01); *A61B 2017/3407* (2013.01); *A61B 2017/3409* (2013.01); *A61B 2090/034* (2016.02)

(58) Field of Classification Search
CPC ............ A61B 17/3403; A61B 17/3494; A61B 2017/00398; A61B 2017/3407; A61B 2017/3409; A61B 2017/3405; A61M 5/427; A61M 2005/3289; A61F 9/0026; A61F 9/00754; A61F 9/00763; A61F 9/013
See application file for complete search history.

(56) References Cited

U.S. PATENT DOCUMENTS

| 4,534,348 A | * | 8/1985 | Fedorov | ............... A61F 9/0133 30/320 |
|---|---|---|---|---|
| 4,834,727 A | | 5/1989 | Cope | |
| 4,960,407 A | | 10/1990 | Cope | |
| 5,014,717 A | | 5/1991 | Lohrmann | |

(Continued)

FOREIGN PATENT DOCUMENTS

| JP | 2009-072221 A | 4/2009 |
|---|---|---|
| JP | 5568016 B2 | 8/2014 |

(Continued)

OTHER PUBLICATIONS

International Search Report and Written Opinion of the International Searching Authority regarding PCT/US2017/018363 dated Jul. 3, 2017; pp. 1-21.

(Continued)

*Primary Examiner* — Martin T Ton
(74) *Attorney, Agent, or Firm* — Armstrong Teasdale LLP (57) ABSTRACT

A surgical device and methods of using the surgical device are disclosed. The surgical device includes a trocar, a cannula releasably mounted on the trocar, and a propulsion system operatively connected to the trocar. The cannula includes a hub, and has a central opening through which the trocar extends. The propulsion system is operable to drive the trocar axially in a forward direction away from a proximal end of the surgical device.

19 Claims, 8 Drawing Sheets

(56) References Cited

U.S. PATENT DOCUMENTS

| | | | |
|---|---|---|---|
| 5,242,427 A | 9/1993 | Bilweis | |
| 5,281,197 A | 1/1994 | Arias et al. | |
| 5,411,511 A | 5/1995 | Hall | |
| 5,611,805 A | 3/1997 | Hall | |
| 5,681,323 A | 10/1997 | Arick | |
| 7,143,926 B2 | 12/2006 | Shelton, IV et al. | |
| 7,364,061 B2 | 4/2008 | Swayze et al. | |
| 8,287,494 B2 * | 10/2012 | Ma | A61F 9/0017 604/151 |
| 8,702,742 B2 | 4/2014 | Hanlon et al. | |
| 9,033,952 B2 | 5/2015 | Chen | |
| 9,072,508 B2 | 7/2015 | Callede et al. | |
| 9,113,856 B2 | 8/2015 | Callede et al. | |
| 9,173,775 B2 | 11/2015 | Haffner et al. | |
| 2001/0008961 A1 * | 7/2001 | Hecker | A61F 9/007 604/117 |
| 2006/0089526 A1 | 4/2006 | Chen et al. | |
| 2006/0089607 A1 | 4/2006 | Chen | |
| 2011/0152774 A1 * | 6/2011 | Lopez | A61B 17/3462 604/165.04 |
| 2012/0271197 A1 * | 10/2012 | Castle | A61B 5/150022 600/583 |
| 2014/0180013 A1 | 6/2014 | Hanlon et al. | |
| 2015/0038893 A1 | 2/2015 | Haffner et al. | |
| 2015/0094751 A1 | 4/2015 | Chen et al. | |
| 2015/0150642 A1 | 6/2015 | Lau et al. | |
| 2015/0351960 A1 | 12/2015 | Cooper | |
| 2016/0015563 A1 * | 1/2016 | Humayun | A61F 9/00736 606/108 |

FOREIGN PATENT DOCUMENTS

| | | |
|---|---|---|
| WO | 0007530 A2 | 2/2000 |
| WO | 2008084063 A1 | 7/2008 |
| WO | 2016010810 A2 | 1/2016 |

OTHER PUBLICATIONS

International Preliminary Report on Patentability of the International Preliminary Examining Authority regarding PCT/US2017/018363 dated Feb. 21, 2018; pp. 1-36.

* cited by examiner

SURGICAL DEVICE WITH TRIGGERED PROPULSION SYSTEM FOR INSERTING A TROCAR-CANNULA ASSEMBLY

FIELD

The field of the disclosure relates generally to a surgical device including a trocar-cannula assembly and, more particularly, to surgical devices including a triggered actuation or propulsion system for precisely inserting the trocar-cannula assembly.

BACKGROUND

In ophthalmic procedures, such as vitrectomies, membranectomies, and photocoagulation, incisions are made in the eye to provide access to the posterior chamber of the eye. Typically, cannulas are inserted into these incisions to keep the incision from closing. Other surgical implements may then be inserted through the cannula into the patient's body after removal of the trocar.

Several studies have been performed to evaluate the success of methods used to gain access to the posterior chamber of the eye. Criteria used to evaluate success include the percentage of self-sealing incisions/wounds immediately after cannula removal, post-operative intraocular pressure maintenance, post-operative pain, incidence of endophthalmitis, time to perform the procedure, and difficulties experienced when performing the procedure.

Variations between surgical procedures, however, have made it more difficult to evaluate and determine optimal surgical techniques and methods, such as insertion angle of the trocar. For example, previous surgical devices used in ophthalmic procedures provide widely varying patient outcomes and recovery times due to variables such as surgical technique, training, or expertise, as well as variance in surgical instruments, including shape, sharpness, and size of trocars and cannulas used in the procedure. Accordingly, an improved surgical device is needed to provide improved and more consistent patient outcomes and recovery times.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

In one aspect, a surgical device is provided. The surgical device includes a trocar, a cannula releasably mounted on the trocar, a propulsion system operatively connected to the trocar, and a positioning member disposed at a distal end of the surgical device. The cannula includes a hub and has a central opening through which the trocar extends. The propulsion system is operable to drive the trocar axially in a forward direction away from a proximal end of the surgical device. The positioning member includes an engagement member having a contoured engagement surface that, when engaged with an eye of a patient, causes the trocar to be oriented relative to the eye at a predetermined oblique entry angle.

In another aspect, a method of using a surgical device to insert a trocar-cannula assembly into eye tissue is provided. The surgical device includes a propulsion system operatively connected to the trocar-cannula assembly, and a positioning member disposed at a distal end of the surgical device. The method includes engaging the eye tissue with the positioning member, where engaging the eye tissue with the positioning member causes the trocar-cannula assembly to be oriented at a predetermined oblique entry angle relative to the eye tissue, activating the propulsion system, and driving the trocar-cannula assembly with the propulsion system into the eye tissue at the predetermined oblique entry angle.

In yet another aspect, a surgical device for incising eye tissue is provided. The surgical device includes a trocar-cannula assembly and a propulsion system operatively connected to the trocar-cannula assembly and operable to drive the trocar-cannula assembly axially in a forward direction away from a proximal end of the surgical device. The trocar-cannula assembly includes a trocar and a cannula releasably mounted on the trocar. The cannula includes a hub and has a central opening through which the trocar extends. The propulsion system is operable to displace the trocar-cannula assembly by a stroke length and stop forward movement of the trocar-cannula assembly prior to the hub of the cannula contacting the eye tissue.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Corresponding reference characters indicate corresponding parts throughout the several views of the drawings.

DETAILED DESCRIPTION

Embodiments of the systems and methods described herein are designed to improve patient outcomes and recovery times following surgical procedures, such as ophthalmic produces, by reducing strain and trauma imparted to tissue during the surgical procedure, and by providing consistent, optimal wound geometries at incision sites. The present disclosure provides examples of surgical devices and methods designed to produce consistent wound geometries and incision entry angles into the eye regardless of varying factors, such as surgeon technique, training, or expertise, and manufacturing variances in surgical instruments, such as the shape, sharpness, and size of trocars and cannulas used in surgical procedures. Additionally, embodiments of the surgical devices and methods described herein facilitate accurate placement of incisions in the Pars Plana for ophthalmic procedures without reliance on additional instrumentation, reduce deflection of the eye during cannula insertion, and reduce the amount of intraocular pressure rise experienced by the eye during cannula insertion.

As noted above, several studies have been performed to evaluate the success of methods used to gain access to the posterior chamber of the eye. One surgical technique that has been shown to improve outcomes in ophthalmic procedures is creation of the sclerotomy at an angle relative to the wall of the sclera. The angled incision allows the positive (relative to atmosphere) pressure inside the eye (i.e., the intraocular pressure) to help close the wound after the instrument cannula is removed. Viewed strictly from an initial ability for the wound to seal, the ideal insertion angle is nearly tangential to the scleral wall. In practice this type of wound is impractical because a small error in the insertion angle can result in the instrument cannula being too short to fully enter the posterior chamber with the accompanying risk of detachment complications when instruments are inserted. In addition, the strain put onto the tissue around the incision is increased as the position of the cannula is twisted to allow instrument access into the various portions of the posterior chamber, which compromises the tissues ability to recover its shape and seal. However, efforts to determine the optimal insertion angle have been complicated by difficulties in consistently controlling the insertion angle of the trocar and cannula. Variations in surgeon technique, instrument quality, instrument design, intraocular pressure, scleral toughness and other variables can all contribute to variation in the incision angle.

Wound geometry has also been shown to influence surgery outcomes. For example, the shape, size, and sharpness of the cutting tip of the trocar determine the shape, length, and quality (e.g., cleanly cut vs. torn) of the resulting wound. Additionally, the shape and length of the wound relative to the outside diameter of the instrument cannula determines the amount of strain applied to the tissue by the instrument cannula. A cleanly cut straight incision that is barely large enough to stretch around the instrument cannula with minimized strain to the surrounding tissue yields optimal results. This type of wound seals well after the instrument cannula is removed, and tends to resist inadvertent cannula removal because of the tension of the tissue around the instrument cannula. Manufacturing variations in trocar sharpness can have a significant effect on how cleanly cut the wound is.

The configuration of the cannula to trocar shaft interface can also influence the ease of cannula insertion, wound geometry, and wound sealing. For example, larger differences between the trocar diameter and the instrument cannula diameter increase the requirements for the tissue to stretch around the cannula. If the tissue is strained beyond its elastic limit, then tearing can occur and both cannula retention and wound sealing are compromised. The shape of the distal end (the end that enters the eye first) of the instrument cannula can ease the initial entry of the cannula into the incision, but has little effect on the ultimate amount of strain caused to the tissue upon cannula insertion.

Variability in manufacturing tolerances, surgeon technique, and instrument designs can lead to a large variance in patient outcomes and surgeon comfort level. For example, a trocar that is less sharp than ideal requires significantly more force to create an incision, and can yield an incision that is less capable of sealing. The increase in force also presents a challenge to the surgeon because the eye tends to push away from the trocar and requires counter force to maintain the desired position during trocar insertion. As the force required for trocar insertion increases, controlling the position of the eye becomes more difficult.

Embodiments of the systems and methods described herein are designed to facilitate reducing strain and trauma imparted to tissue during surgical procedures, and to facilitate consistent, optimal wound geometries at incision sites. In particular, the present disclosure provides example surgical devices and methods that include a triggered drive or propulsion system configured to drive a trocar-cannula assembly with a force and velocity greater than that practically achievable by manual manipulation. The force and velocity imparted to the trocar-cannula assembly is sufficiently high such that the inertia of the tissue incised by the trocar is not overcome to a significant degree by the force generated during the creation of the incision and subsequent insertion of the cannula. Additionally, the system is operable to precisely control the stroke length of the trocar-cannula assembly to enable optimal insertion of the trocar-cannula assembly without exerting excessive pressure on the tissue in which the trocar-cannula assembly is inserted, and without inserting the assembly to less than or greater than optimal depth. For example, in some embodiments, the propulsion system is configured to stop the trocar-cannula assembly at a point just prior to a hub of the cannula contacting the tissue into which the trocar is inserted. Additionally, embodiments of the surgical devices and methods described herein utilize a positioning member to facilitate consistent positioning and orientation of the trocar prior to insertion of the trocar at the surgical site. The positioning member thereby facilitates producing consistent wound geometries and incision entry angles into the eye regardless of varying factors, such as surgeon technique, training, or expertise.

Figure 1:
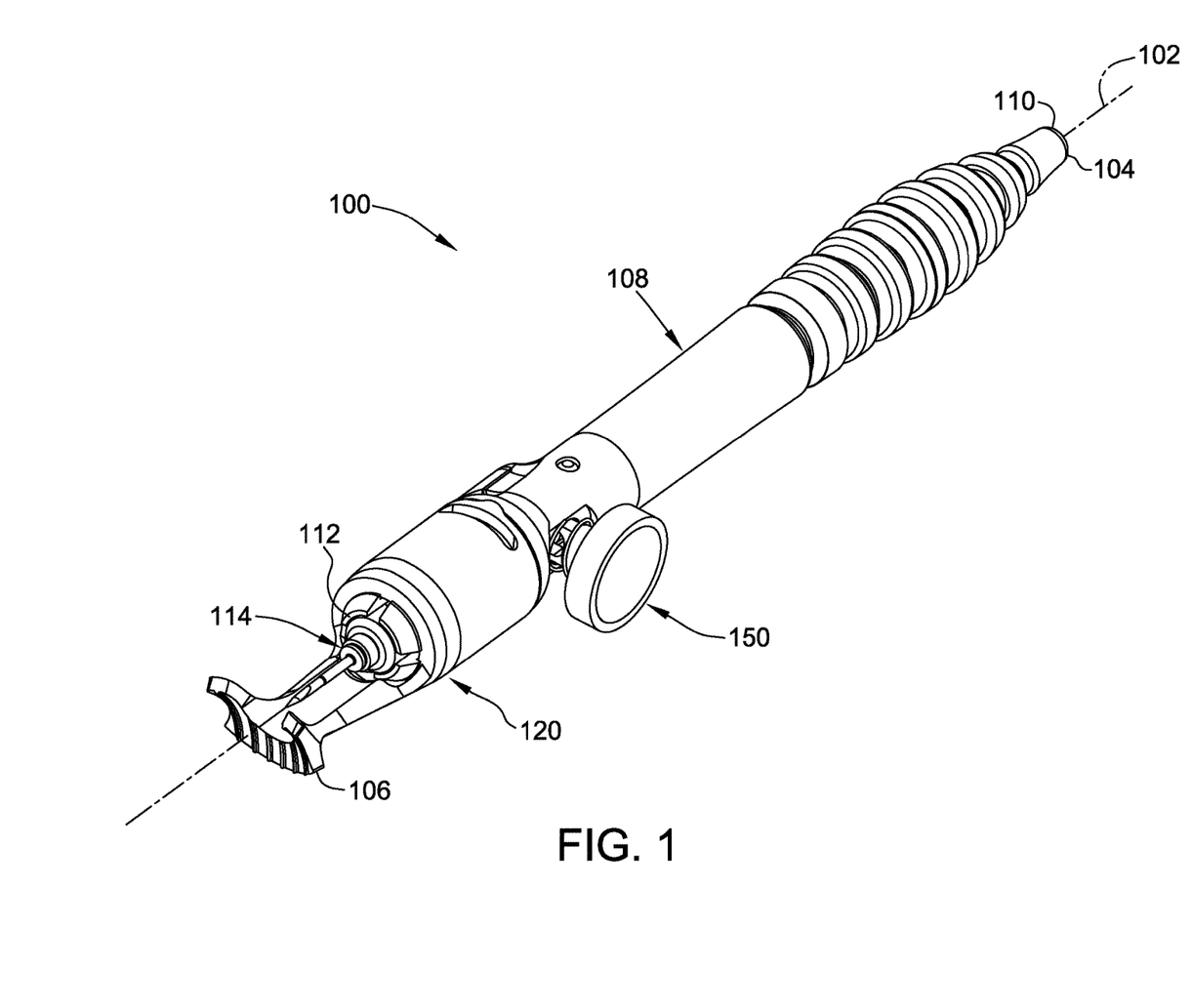
FIG. 1 is a perspective of one embodiment of a surgical device including a propulsion or actuation system for inserting a trocar-cannula assembly into a patient.
Figure 2:
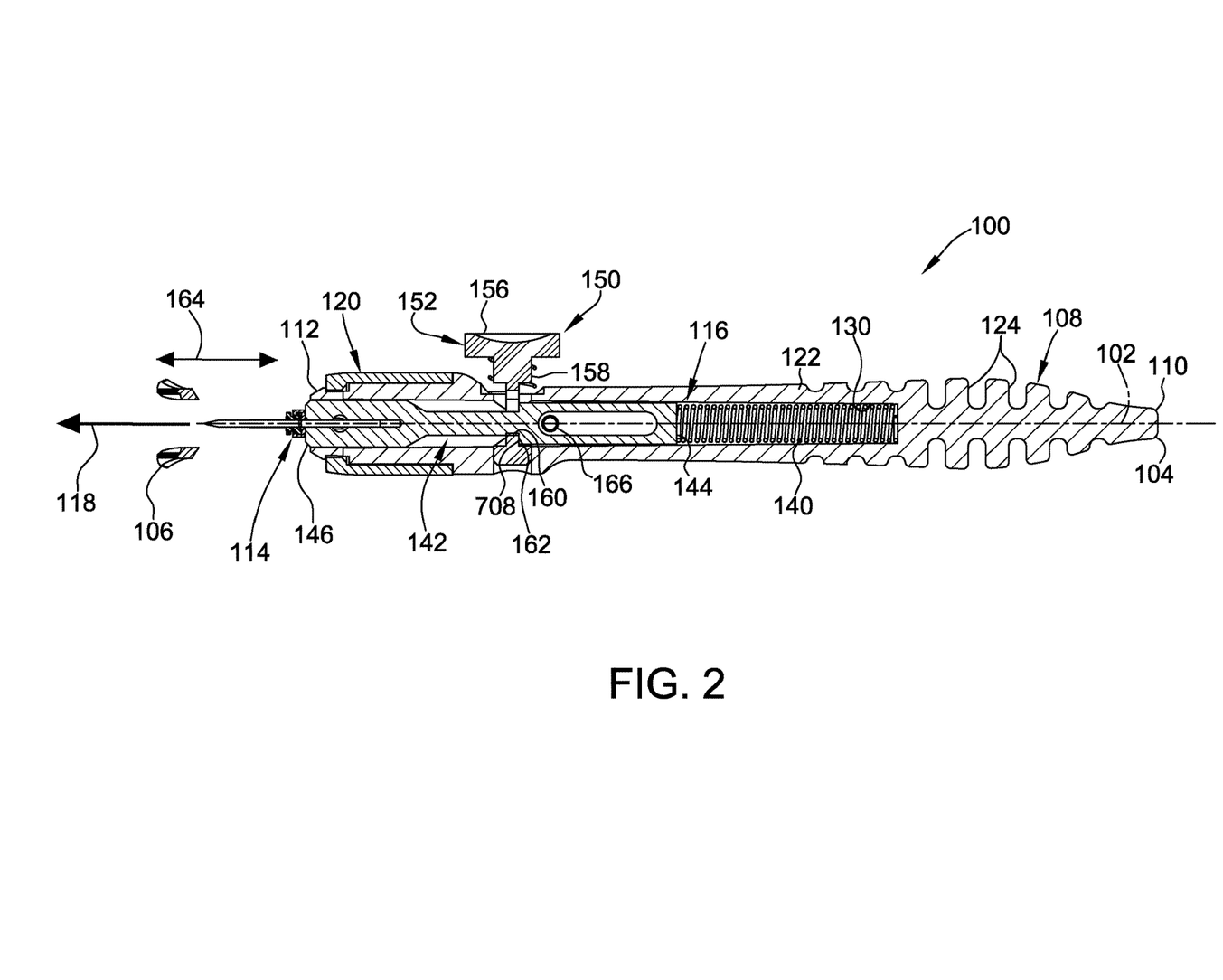
FIG. 2 is a cross-sectional view of the surgical device of FIG. 1.
Figure 3:
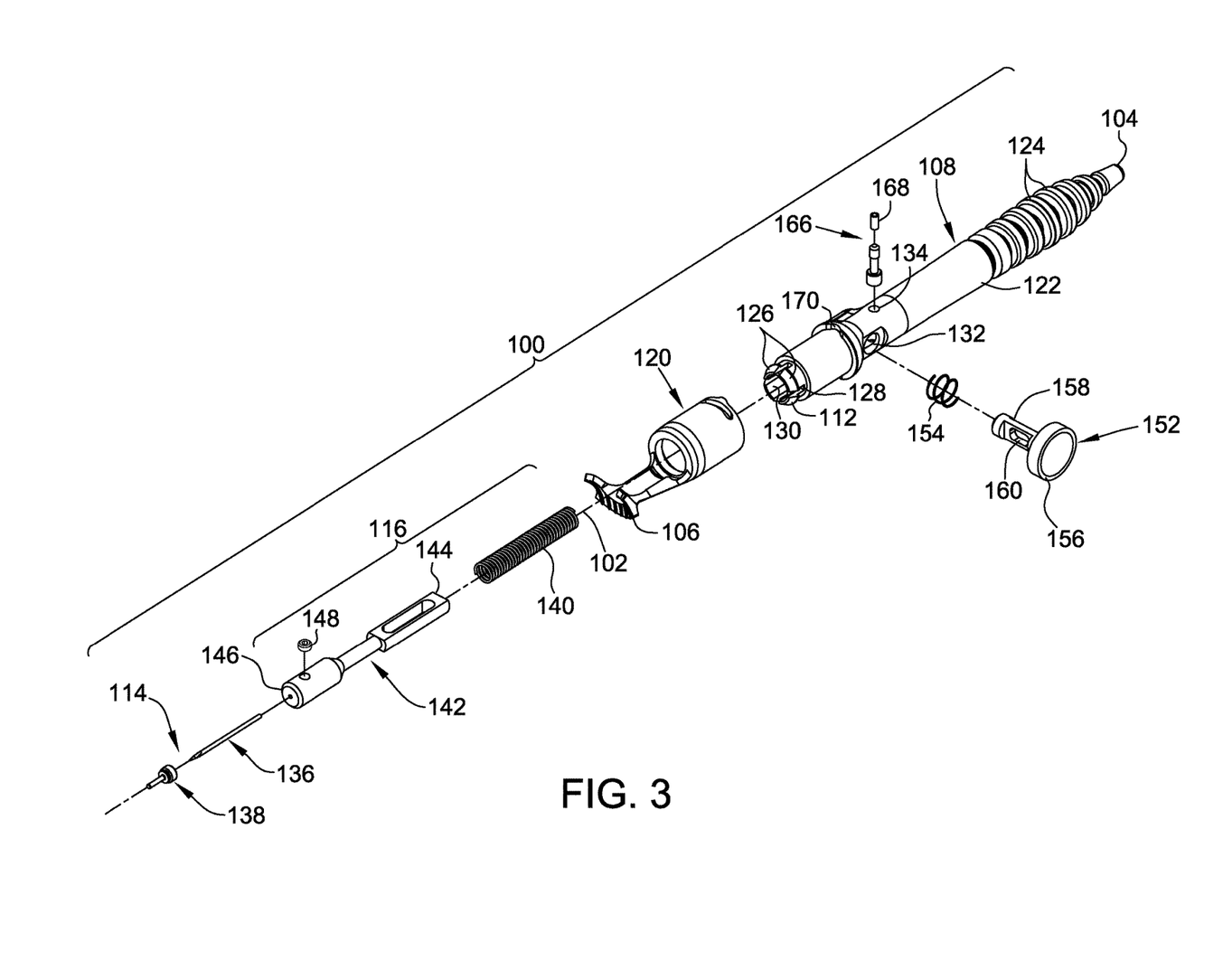
FIG. 3 is an exploded view of the surgical device of FIG. 1.

FIG. 1 is a perspective view of a surgical device 100 including a triggered drive system (may also be referred to as a propulsion system or an autoinserter) for driving a trocar-cannula assembly into a tissue or organ. FIG. 2 is a cross-section of the surgical device 100, and FIG. 3 is an exploded view of the surgical device 100. As shown in FIGS. 1-3, the surgical device 100 extends a length along a central longitudinal axis 102 from a first, proximal end 104 to a second, distal end 106. The surgical device 100 generally includes a handle 108 having a proximal end 110 and an opposing distal end 112, a trocar-cannula assembly 114 disposed at the distal end 112 of the handle 108, and a propulsion system 116 configured to axially drive or propel the trocar-cannula assembly 114 in a forward direction (i.e., away from the proximal end 110 of the handle 108) indicated by arrow 118 in FIG. 2. The surgical device also includes a positioning member 120 disposed at the distal end 112 of the handle 108. The positioning member 120 is configured to facilitate alignment of the surgical device 100 relative to a patient's eye, and stabilize the surgical device 100 during surgical procedures.

The surgical device 100 may be used in various surgical procedures. In the example embodiment, the surgical device 100 is particularly suitable for use in ophthalmic procedures including, for example and without limitation, vitrectomies, membranectomies, and photocoagulation. The surgical device 100 may be used, for example, to incise the sclera of a patient's eye, and to insert the trocar-cannula assembly 114 through the sclera to provide access to the posterior segment of the eye. In the example embodiment, the surgical device 100 is particularly suited for use on humans, although in other embodiments, the surgical device 100 may be modified for non-human use, such as for veterinary procedures.

The handle 108 includes a generally cylindrical body 122 extending from the distal end 112 of the handle 108 to the proximal end 110 of the handle 108. The body 122 of the handle 108 is ergonomically shaped to facilitate gripping and manipulation of the surgical device 100. In the illustrated embodiment, the handle 108 includes tactile ridges 124 to further facilitate gripping and manipulation of the surgical device 100. In the illustrated embodiment, the tactile ridges 124 are disposed between a midpoint of the handle 108 and the proximal end 110 of the handle 108, although other embodiments may include tactile ridges located at other locations along the handle 108. In yet other embodiments, the handle 108 may not include any tactile ridges.

The handle 108 also includes a plurality of retention tabs 126 securing the positioning member 120 to the distal end 112 of the handle 108. The retention tabs 126 are disposed at the distal end 112 of the handle 108, and are circumferentially spaced about the longitudinal axis 102 of the surgical device 100. Adjacent retention tabs 126 are separated from one another by a slit 128 extending axially into the handle 108 from the distal end 112. The retention tabs 126 are configured to deflect radially inward as the positioning member 120 is slid over the distal end 112 of the handle 108, and return to their initial, undeflected position (shown in FIGS. 2 and 3) to inhibit axial movement of the positioning member 120.

As shown in FIG. 2, the body 122 of the handle 108 defines a cavity 130 in which components of the propulsion system 116 are housed. The cavity 130 is suitably sized and shaped to permit components of the propulsion system 116 to be housed therein. In the illustrated embodiment, the cavity 130 has a circular cross-section, and is configured to permit axially movement of components of the propulsion system 116 therethrough.

In the illustrated embodiment, the body 122 also defines a pair of triggering device openings 132 and a pair of stop pin openings 134. Each of the triggering device openings 132 and the stop pin openings 134 extends radially through the body 122 of the handle 108. Further, each of the triggering device openings 132 is located on a diametrically opposite side of the body 122 from the other of the triggering device openings 132, and each of the stop pin openings 134 is located on a diametrically opposite side of the body 122 from the other of the triggering device openings 132. The triggering device openings 132 are suitably sized and shaped to receive at least a portion of a triggering device, described in more detail herein. The stop pin openings 134 are suitably sized and shaped to receive at least a portion of a stop pin, described in more detail herein.

The handle 108 can be constructed of suitably rigid or semi-rigid materials, including, for example and without limitation, plastics, polymers, metals, composites, and combinations thereof. In certain embodiments, portions of the handle 108 may be constructed of a flexible material, including, for example and without limitation, silicone or similar elastomeric or flexible polymers.

Figure 4:
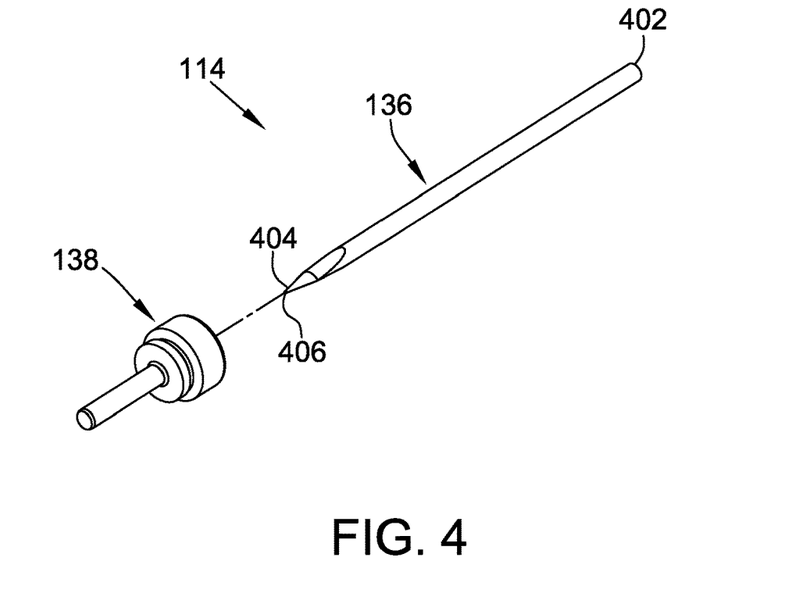
FIG. 4 is an exploded view of the trocar-cannula assembly of the surgical device of FIG. 1, the trocar-cannula assembly including a trocar and a cannula.

The trocar-cannula assembly 114 includes a trocar 136 and a cannula 138 releasably mounted on the trocar 136. FIG. 4 is an enlarged exploded view of the trocar-cannula assembly 114. As shown in FIG. 4, the trocar 136 has a proximal end 402 and a distal end 404. The distal end 404 of the trocar 136 includes a cutting tip 406 for piercing or incising organs or tissue, such as the sclera of an eye. The cutting tip 406 may be beveled, tapered, and/or sharpened to facilitate insertion of the trocar 136. Suitable configurations for the trocar 136 include hypodermic needles, lancet-shaped needles, stiletto blades, saber-tipped blades, beveled rods, and any other configuration suitable for making a stab incision in a tissue or organ. The trocar 136 may be constructed of suitably rigid materials, including, for example and without limitation, stainless steel. In some embodiments, the trocar 136 is sized for use in ophthalmic surgical procedures. For example, the trocar 136 may have an outer diameter of between about 20-gauge (0.91 mm) and about 27-gauge (0.41 mm). In some embodiments, the trocar 136 has an outer diameter less than or equal to 23-gauge (0.64 mm), less than or equal to 25-gauge (0.51 mm), or even less than or equal to 27-gauge. In other embodiments, the trocar 136 may have an outer diameter greater than 20-gauge.

Figure 5:
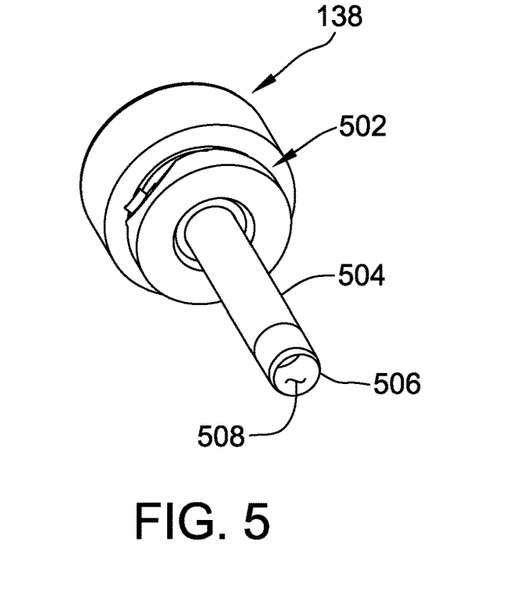
FIG. 5 is a perspective of the cannula of the trocar-cannula assembly of FIG. 4.

FIG. 5 is an enlarged perspective view of the cannula 138. As shown in FIG. 5, the cannula 138 includes an annular flange or hub 502 and a hollow shaft 504 extending from the hub 502 to a distal end 506 of the cannula 138. The shaft 504 defines a central opening 508 sized and shaped to receive the trocar 136 therein. The inner diameter of the cannula shaft 504 may be sized just larger than an outer diameter of trocar 136 to minimize the step (i.e., the difference in diameters) between the trocar 136 and the cannula 138. Minimizing or limiting the change in diameter from the trocar 136 to the cannula 138 facilitates insertion of the trocar-cannula assembly 114 into tissue, and minimizes or limits the strain on the tissue during insertion. In some embodiments, the inner diameter of the cannula shaft 504 is between about 20-gauge and about 27-gauge. In some embodiments, the inner diameter of the cannula shaft 504 is less than or equal to 23-gauge, less than or equal to 25-gauge, or even less than or equal to 27-gauge. In other embodiments, the inner diameter of the cannula shaft 504 is greater than 20-gauge. In some embodiments, a portion of the cannula shaft 504 (such as the distal end) is swaged or tapered radially inward to a diameter substantially equal to the diameter of the trocar 136. In such embodiments, the cannula 138 may be press fit onto the trocar 136 to provide the minimal amount of friction between the cannula 138 and trocar 136 needed to maintain the position of the cannula 138 on the trocar 136 when the propulsion system 116 is activated.

The cannula 138 may be constructed of rigid materials, including, for example and without limitation, stainless steel, titanium, and combinations thereof. Additionally or alternatively, the cannula 138 may be constructed of flexible materials, including, for example and without limitation, plastics, such as polyamide. The cannula 138 may be constructed of the same materials as the trocar 136, or the cannula 138 may be constructed of different materials than the trocar 136.

Figure 6:
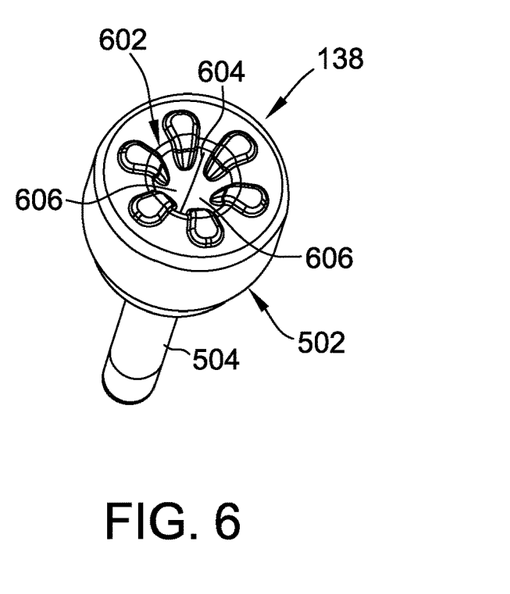
FIG. 6 is another perspective of the cannula of FIG. 5 showing a valve of the cannula.

In some embodiments, such as the embodiment illustrated in FIG. 6, the cannula 138 includes a valve 602 to restrict fluid flow through the cannula 138 (specifically, through the central opening 508). In the illustrated embodiment, the valve 602 is made of or includes a flexible, resilient material, including, for example and without limitation, silicone. Other suitable materials from which the valve 602 may be made of include, for example and without limitation, polyurethane, PVC, and other medical grade elastomers. The valve 602 has a slit 604 defined therein to allow insertion of the trocar 136 (and other surgical instruments) therethrough. The slit 604 defines two valve members 606 that deflect from an initial position (shown in FIG. 6) when the trocar 136 is inserted through the valve 602. When the trocar 136 is removed from the valve 602, the valve members 606 return to the initial position, and seal the cannula opening 508 to inhibit fluid flow therethrough. In the illustrated embodiment, when the trocar-cannula assembly 114 is assembled, the valve members 606 are biased against and engage the trocar 136, and provide a resistive frictional force sufficient to maintain the position of the cannula 138 relative to the trocar 136. The valve 602 and trocar 136 are constructed of materials with suitable coefficients of friction such that the resistive frictional forces between the valve 602 and the trocar 136 are sufficient to maintain the position of the cannula 138 on the trocar 136 when the propulsion system 116 is activated. In some embodiments, for example, the valve is constructed of silicone, and the trocar is constructed of stainless steel.

The propulsion system 116 is operatively connected to the trocar-cannula assembly 114, and is configured to propel or drive the trocar-cannula assembly 114 in the forward direction 118 when activated by a user of the surgical device 100. The propulsion system 116 can include any suitable electrical, mechanical, and/or electromechanical devices for generating and/or transmitting kinetic energy to the trocar-cannula assembly 114 to drive the trocar-cannula assembly 114 in the forward direction 118. In some embodiments, the propulsion system 116 includes at least one spring-driven piston. In some embodiments, the propulsion system 116 may include a pneumatically-driven piston and/or a hydraulically-driven piston. In some embodiments, the propulsion system 116 may include one or more diaphragms driven by a spring, a pneumatic system, or a hydraulic system. In some embodiments, the propulsion system 116 may include a solenoid assembly including, but not limited to, a solenoid coil and a piston, and a rotary solenoid and a transmission member to convert rotational motion of the rotary solenoid to linear motion. In some embodiments, the propulsion system 116 may include an electric motor and a suitable transmission member to transmit motion from the motor to the trocar-cannula assembly 114. Suitable transmission members include, but are not limited to, worm gear drives and rack and pinion assemblies. Other devices suitable for use in or as a propulsion system include, but are not limited to, speaker coils, electromagnets, permanent magnets, shape memory alloys, and piezoelectric materials.

In some embodiments, the propulsion system 116 generally includes a drive member configured to generate kinetic energy, and a transmission member configured to transmit the kinetic energy from the drive member to the trocar-cannula assembly 114. In the illustrated embodiment, the propulsion system 116 includes a drive member in the form of a helical spring 140, and a transmission member in the form of a piston 142. In some embodiments, such as the embodiment illustrated in FIGS. 2 and 3, the propulsion system 116 is configured (e.g., sized and shaped) to fit within the cavity 130 of the handle 108. In other embodiments, components of the propulsion system 116 may be integrated within the body 122 of handle 108, and/or coupled to the body 122 of handle 108.

As shown in FIG. 2, the spring 140 is disposed within the cavity 130 defined by the body 122, and is compressible between the piston 142 and the proximal end 110 of the handle 108. The piston 142 is axially moveable under the force of the spring 140 between a first, retracted position (shown in FIG. 2), and a second, extended position (shown in FIGS. 9 and 10). The piston 142 is connected to the spring 140 at a first, proximal end 144 of the piston 142, and is connected to the trocar-cannula assembly 114 at a second, distal end 146 of the piston 142.

Figure 7:
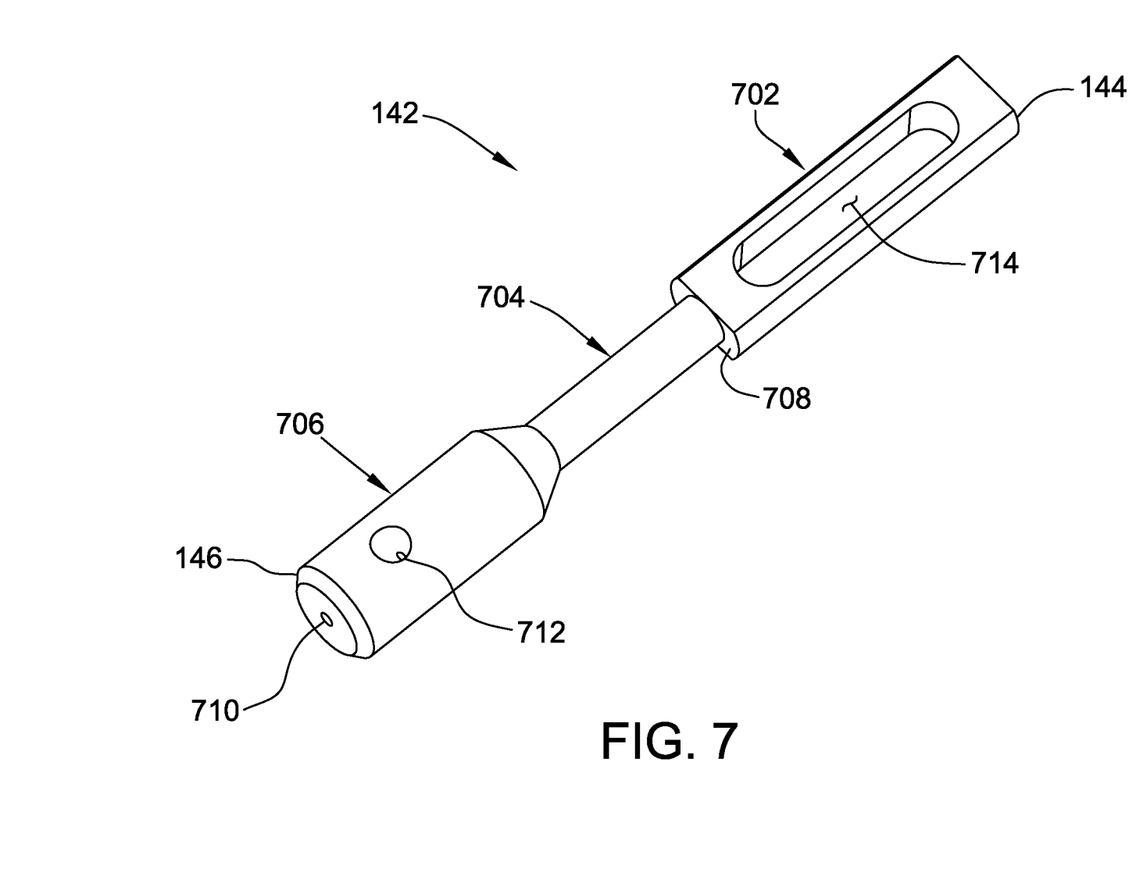
FIG. 7 is a perspective of a piston suitable for use in the propulsion system of the surgical device of FIG. 1.

FIG. 7 is a perspective view of the piston 142 from the propulsion system 116. As shown in FIG. 7, the piston 142 includes a first portion 702, a second portion 704, and a third portion 706. The first portion 702 has rectangular or pseudo-rectangular cross-section, and has a width or diameter greater than the second portion 704. The first portion 702 adjoins the second portion 704 at a lip 708. The second portion 704 has a substantially circular cross-section, and has a width or diameter less than each of the first portion 702 and the third portion 706. The second portion 704 is disposed between and interconnects the first portion 702 and the third portion 706.

The third portion 706 of the piston 142 is configured for connection to the trocar-cannula assembly 114 to secure the trocar-cannula assembly 114 to the piston 142, and is also referred to herein as a trocar holder. In the illustrated embodiment, the third portion 706 includes a trocar opening 710 extending axially into the piston 142 from the distal end 146. The trocar opening 710 is sized and shaped to receive the trocar 136 therein. The third portion 706 also includes a fastener opening 712 extending radially into and through the piston 142. The fastener opening 712 is sized and shaped to receive a fastener, such as a set screw, therein to secure the trocar 136 to the third portion 706 of the piston 142. When the surgical device 100 is assembled, the proximal end 402 of the trocar 136 extends into the trocar holder 706, and is fixed to the trocar holder 706 by suitable connection means. In the illustrated embodiment, the trocar 136 is secured to the trocar holder 706 with a set screw 148 (shown in FIG. 2). In other embodiments, the trocar 136 may be secured to the trocar holder 706 using any suitable connection means that enables the surgical device 100 to function as described herein. In some embodiments, for example, the trocar holder 706 may be over-molded onto the trocar 136. In yet other embodiments, the trocar 136 and the trocar holder 706 may be formed as a single, integral piece, for example, by casting or molding.

In the illustrated embodiment, the first portion 702 of the piston 142 has an elongate slot 714 defined therein. The slot 714 is elongate in the direction of motion of the propulsion system 116, which, in the illustrated embodiment, is parallel to the longitudinal axis 102 of the surgical device 100. The elongate slot 714 is sized and shaped to receive a stop pin therein to control a stroke length of the propulsion system 116, as described in more detail herein.

As noted above, the propulsion system 116 is configured to drive or propel the trocar-cannula assembly 114 with a force and velocity greater than that typically applied by manual manipulation. In particular, the propulsion system 116 is configured to drive the trocar 136 and cannula 138 with a sufficient force and velocity such that the inertia of the tissue incised by the trocar 136 is not overcome to a significant degree by the force generated during the creation of the incision and subsequent insertion of the cannula 138. As a result, production tolerances or imperfections in the cutting tip 406 of the trocar 136 have less of an effect on the wound geometry because the tissue inertia tends to greatly increase the stress transmitted to the tissue as compared to a manual incision with the same trocar. The propulsion system 116 thereby provides a cleaner cut as compared to manually inserted trocars, and imparts less stress to surrounding tissue (outside the area of the incision) as compared to manually inserted trocars. Additionally, because the tissue moves less during the insertion, the intraocular pressure is affected to a much lower degree than with the manually inserted trocars.

The surgical device 100 also includes a trigger or activation device 150 operable to activate the propulsion system 116 in response to user input. Although the activation device 150 is shown as being directly connected to the surgical device 100 in the illustrated embodiment, the activation device 150 may be located remotely from the surgical device 100 in other embodiments. In such embodiments, the activation device 150 may communicate with an electromechanical device operatively connected to the propulsion system 116 to activate the propulsion system 116.

In the illustrated embodiment, the activation device 150 is a manually actuated trigger mechanism. Specifically, the activation device 150 includes a depressible knob or trigger 152 moveable between a first, undepressed position and a second, depressed position, and a helical trigger spring 154 configured to bias the trigger 152 towards the first position. The trigger 152 includes a head 156 connected to a shaft 158 that extends radially through the handle 108 (specifically, through the triggering device openings 132). The head 156 has an enlarged, pronounced diameter relative to the shaft 158 to provide an adequate area for a user to engage and depress the trigger with a thumb or finger. The trigger spring 154 is disposed between the head 156 of the trigger 152 and a radial outer surface of the body 122 to bias the trigger 152 in a radially outward direction.

The trigger 152 has a piston opening 160 defined therein sized and shaped to receive a portion of the piston 142 therein. In the illustrated embodiment, the piston opening 160 has a cross-section sized and shaped complementary to the first portion 702 of the piston 142 to permit the first portion 702 of the piston 142 to pass therethrough. As shown in FIG. 2, when the trigger 152 is in the first position, the piston opening 160 is offset or out of alignment with the first portion 702 of the piston 142. A portion of the shaft 158 engages the lip 708, and acts as a latch 162 to inhibit forward axial movement of the piston 142. When the trigger is depressed from the first position to the second position, the piston opening 160 is aligned with the first portion 702 of the piston 142, and the latch 162 disengages the lip 708, allowing the piston 142 to move axially forward under the force of the spring 140.

Figure 9:
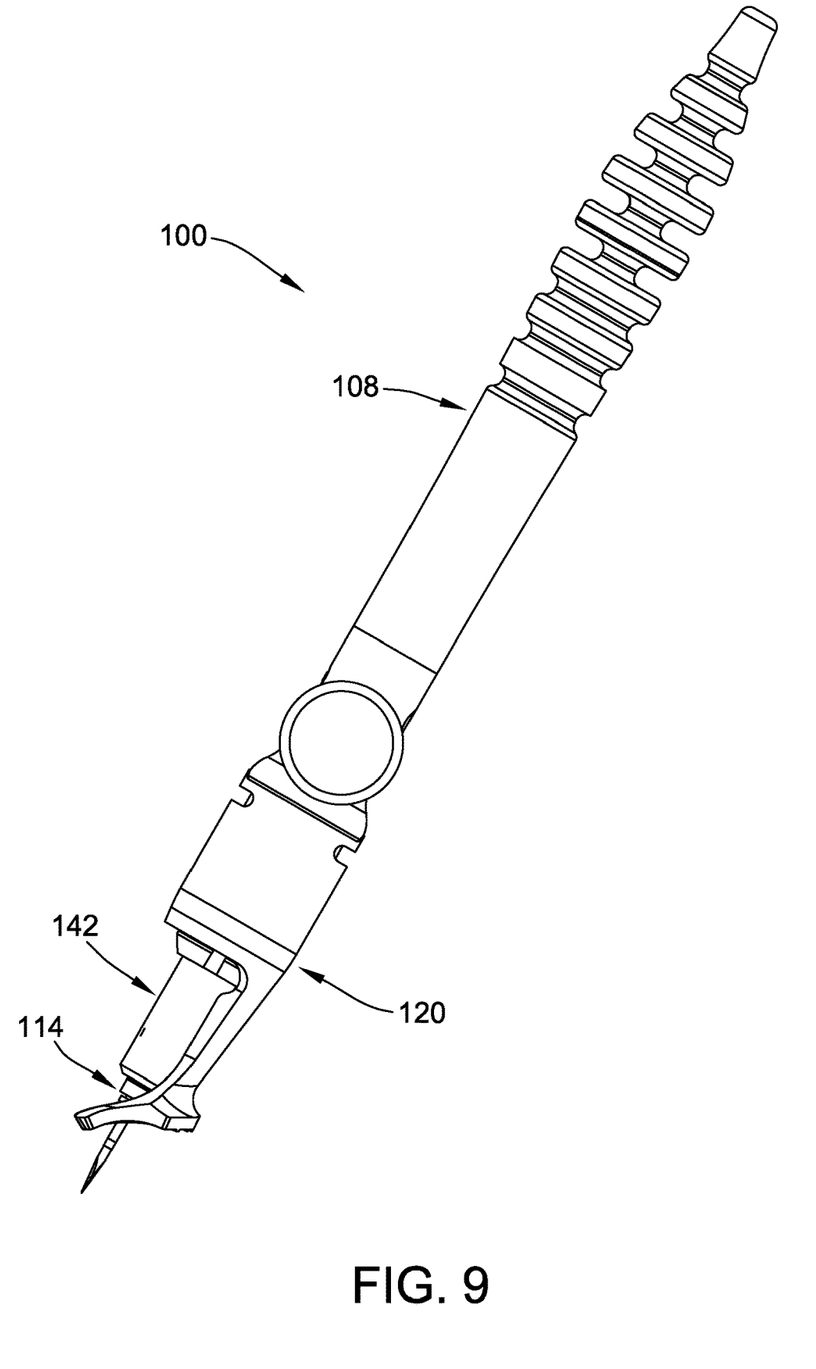
FIG. 9 is a side view of the surgical device of FIG. 1 showing the trocar-cannula assembly in an extended position.
Figure 10:
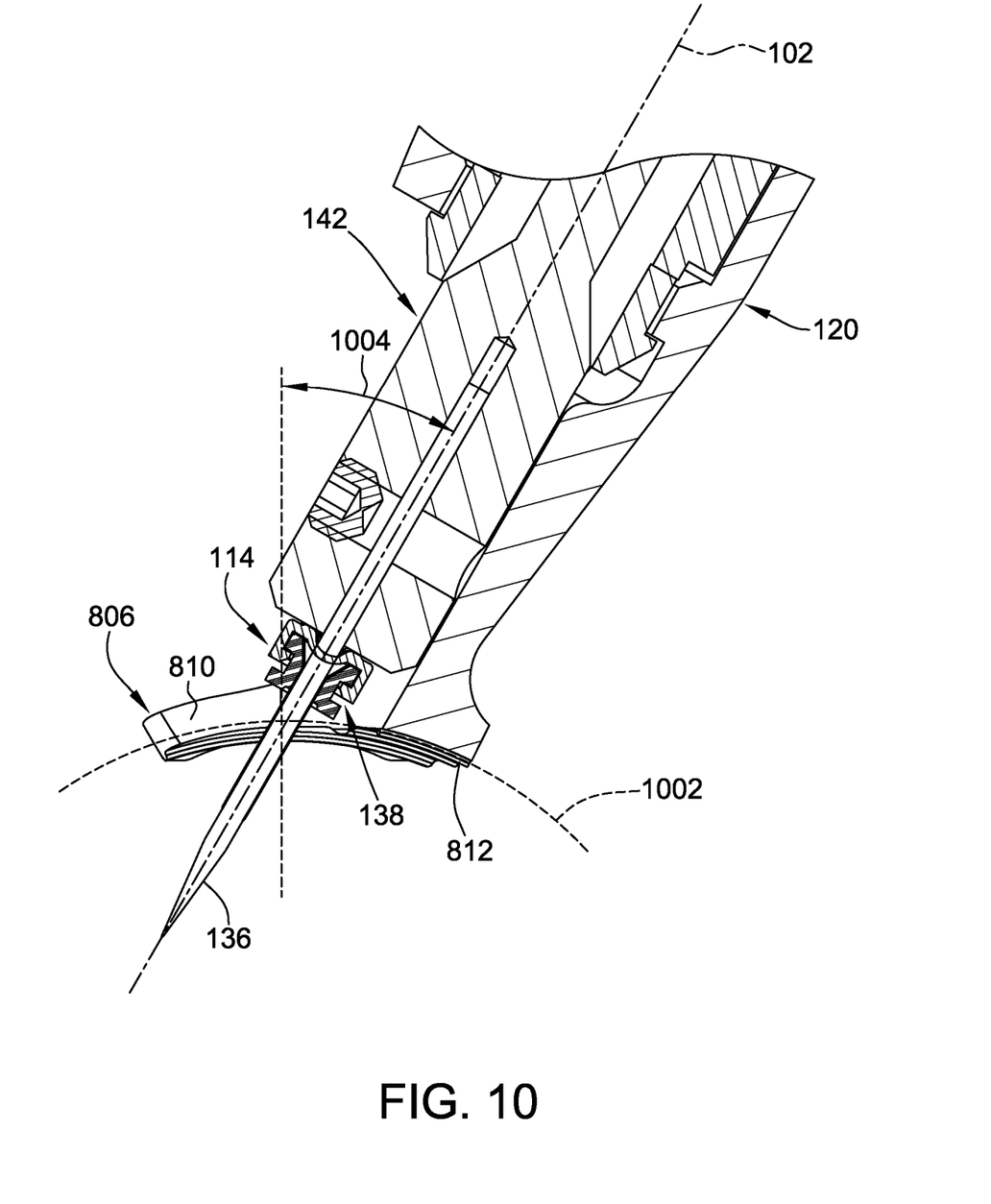
FIG. 10 is an enlarged cross-sectional view of the surgical device of FIG. 9.

The propulsion system 116 is configured to move the trocar-cannula assembly 114 axially in the forward direction 118 a stroke length 164, measured as the axial displacement of the trocar-cannula assembly 114 between the initial, unfired position (shown in FIG. 1), and the extended, fired position (shown in FIGS. 9 and 10). The propulsion system 116 is configured to provide an optimal stroke length 164 of the trocar-cannula assembly 114 to enable optimal insertion of the trocar-cannula assembly 114 without exerting excessive pressure on the tissue in which the trocar-cannula assembly 114 is inserted. In particular, the propulsion system 116 is configured to stop the trocar-cannula assembly 114 just prior to the hub 502 of the cannula 138 contacting the tissue into which the trocar 136 is inserted. In the illustrated embodiment, the propulsion system 116 includes a stop pin 166 configured to limit and precisely control the stroke length 164 of the trocar-cannula assembly 114.

The stop pin 166 is positioned within the stop pin openings 134 defined by the body 122 of the handle 108, and extends radially through the body 122. When the surgical device 100 is assembled, the stop pin 166 is positioned within the slot 714 defined by the first portion 702 of the piston 142. The stop pin 166 is configured to engage the piston 142 to limit axial movement of the piston 142. Specifically, the stop pin 166 is configured to engage the first portion 702 of the piston 142 along inner surfaces of the piston 142 that define the slot 714. The slot 714 has a length substantially equal to the stroke length 164 of the trocar-cannula assembly 114. As shown in FIG. 3, the stop pin 166 includes a bearing collar or sleeve 168 to minimize or limit friction between the stop pin 166 and the piston 142.

As noted above, the propulsion system 116 is configured to drive or propel the trocar-cannula assembly 114 with a force and velocity greater than that typically applied by manual manipulation. The propulsion system 116 may be configured to complete a stroke length of the trocar-cannula assembly 114 within a certain amount of time, such as within 1 second, within 0.5 seconds, or even within 0.1 seconds. Further, in some embodiments, the propulsion system 116 may be configured to move the trocar-cannula assembly 114 at a certain velocity, such as between 0.05 m/s and 1 m/s, or between 0.1 m/s and 1 m/s. In other embodiments, the propulsion system 116 may be configured to move the trocar-cannula assembly 114 at a velocity less than 0.05 m/s, or at a velocity greater than 1 m/s.

Figure 8:
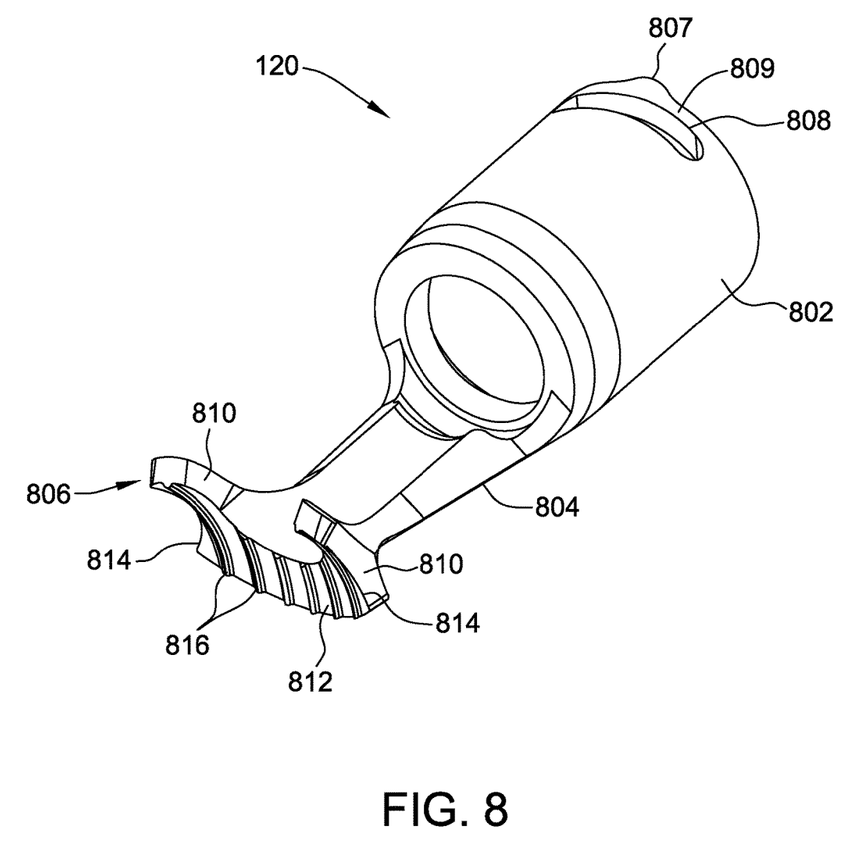
FIG. 8 is a perspective of a positioning member of the surgical device of FIG. 1.

Referring again to FIGS. 1-3, the positioning member 120 is configured to engage a generally spherical surface, such as the sclera of an eye, to align the surgical device 100 (specifically, the trocar-cannula assembly 114) with a desired incision site on the eye, and to stabilize the surgical device 100 during activation of the propulsion system 116. FIG. 8 is a perspective view of the positioning member 120 shown in FIGS. 1-3. As shown in FIG. 8, the positioning member 120 generally includes a connector portion 802 configured for connection to the distal end 112 of the handle 108, a leg 804 extending distally from the connector portion 802, and an engagement member 806 disposed at a distal end of the leg 804.

The connector portion 802 is configured for connection to the handle 108 to fix the positioning member 120 relative to the handle 108. In the illustrated embodiment, the connector portion 802 is a sleeve having an inner diameter sized and shaped to receive the distal end 112 of the handle 108 therein. When the surgical device 100 is assembled, a distal end of the connector portion 802 engages the retention tabs 126 of the handle 108, and a proximal end of the connector portion engages a lip on the handle 108 to prevent axial movement of the positioning member 120 relative to the handle 108. In other embodiments, the connector portion 802 may include any suitable connecting structure that enables the connector portion 802 to connect to the handle, including, for example and without limitation, threads.

The connector portion 802 also has a pair of alignment protrusions 807 disposed diametrically opposite one another on the connector portion 802. Only one of the alignment protrusions 807 is shown in FIG. 8. The alignment protrusions 807 are configured to align the positioning member 120 relative to the handle 108 and/or the activation device 150 when the positioning member 120 is connected to the handle 108. Specifically, in the example embodiment, each of the alignment protrusions 807 is configured to align with one of two alignment recesses 170 (shown in FIG. 3) defined by the body 122 of the handle 108 when the positioning member 120 is connected to the handle 108. The alignment protrusions 807 and the alignment recesses 170 permit two rotational positions of the positioning member 120 relative to the handle 108 when the positioning member 120 is connected to the handle 108. The two rotational positions allow a user of the surgical device 100 to selectively orient the positioning member 120 in one of the two rotational positions to enable selective use of a finger or a thumb to actuate the activation device 150.

In the example embodiment, each of the alignment protrusions 807 is located along a portion of the connecter portion 802 defined by one of two circumferentially extending slots 808 located diametrically opposite one another on the connector portion 802. Only one of the slots 808 is shown in FIG. 8. Each of the slots 808 defines an arm 809 at a proximal end of the connector portion 808. The slots 808 enable deflection of the arms 809 as the positioning member 120 is inserted over the distal end 112 of the handle 108, causing the arms 809 to behave like a spring and bias the alignment protrusions 807 into engagement with the alignment recesses 170.

The leg 804 extends distally from the connector portion 802, and provides a rigid structural connection between the engagement member 806 and the connector portion 802. The leg 804 is sufficiently rigid to inhibit flexing or bending of the positioning member 120 when the engagement member 806 is pressed against a patient's eye and the leg 804 is placed under compression. In the illustrated embodiment, the leg 804 has an arcuate or semi-circular cross-section, although in other embodiments, the leg 804 may have any suitable configuration that enables the positioning member 120 to function as described herein. Further, in the illustrated embodiment, the leg 804 extends only partially around (i.e., in a circumferential direction) the longitudinal axis 102 of the surgical device 100. The leg 804 thereby defines a viewing opening or window that provides direct line-of-sight to the trocar-cannula assembly 114 and the desired incision site. In other embodiments, the leg 804 may extend substantially or entirely around the longitudinal axis 102 of the surgical device 100. In such embodiments, the leg 804 may be constructed of a transparent material to enable line-of-sight to the trocar-cannula assembly 114 and the desired incision site.

The engagement member 806 is disposed at the distal end of the leg 804, and is configured to engage a generally spherical surface, such as the sclera of a patient's eye, to facilitate alignment and positioning of the surgical device 100 during surgical procedures. Specifically, the engagement member 806 includes alignment feet 810 and an engagement surface 812.

As shown in FIG. 8, each alignment foot 810 includes an outer alignment edge 814 that adjoins the engagement surface 812. The alignment edge 814 is shaped complementary to anatomical features of the body to facilitate alignment of the surgical device 100 with a desired incision site. In the illustrated embodiment, the alignment edge 814 is shaped complementary to the corneal limbus of the eye, and has an arcuate shape that is convex with respect to the longitudinal axis 102 of the surgical device 100. In the illustrated embodiment, the alignment edge 814 has a suitable radius of curvature to permit general alignment of the alignment edge 814 with the limbus of the eye. In some embodiments, the alignment edge 814 may have a radius of curvature in a range of 5.0 mm and 7.0 mm, or in a range of 5.4 mm to 6.4 mm. In some embodiments, the alignment edge 814 has a radius of curvature of about 6.0 mm, which corresponds to the radius of curvature of the corneal limbus in an average human adult eye. In other embodiments, the alignment edge 814 may have a radius of curvature less than 5.0 mm, or greater than 7.0 mm (e.g., when used for veterinary procedures).

The alignment edge 814 is spaced radially outward from the central longitudinal axis 102 of the surgical device 100. In the illustrated embodiment, each alignment edge 814 is spaced from the central longitudinal axis 102 of the surgical device 100 by a suitable distance such that, when the alignment edge 814 of one of the alignment feet 810 is aligned with the limbus of the eye, the projected incision site of the trocar-cannula assembly 114 is a predetermined radial distance away from the limbus. The radial spacing between the alignment edges 814 and the longitudinal centerline of the surgical device 100 generally corresponds to the spacing between the limbus and the Pars Plana of the eye. The positioning member 120 of the illustrated embodiment thereby facilities alignment of the trocar-cannula assembly 114 with the Pars Plana of the eye.

The engagement surface 812 is the distal-most surface of the surgical device 100, and is disposed for engagement with the tissue or organ to be incised with the surgical device 100. In the illustrated embodiment, the engagement surface 812 is partially defined by the bottom surfaces of the alignment feet 810.

FIG. 9 is a side view of the surgical device 100 with the trocar-cannula assembly 114 and the piston 142 in the extended position (i.e., after the propulsion system 116 has been activated). FIG. 10 is an enlarged cross-sectional view of the surgical device 100 shown in FIG. 9. In FIG. 10, the propulsion system 116 has been activated, and the trocar-cannula assembly 114 is shown as being inserted into a patient's eye, indicated by the dotted line 1002. As shown in FIG. 10, the engagement surface 812 is configured to orient the surgical device 100 (specifically, the trocar 136) at a predetermined oblique entry angle 1004 when the engagement surface 812 is positioned flush with the tissue or organ to be incised with the surgical device 100. The entry angle 1004 may be defined as the angle of incidence between the trocar 136 and the normal or perpendicular line of the surface incised by the trocar 136 at the point of insertion. In the illustrated embodiment, the engagement surface 812 is configured to orient the surgical device 100 at an optimal entry angle for incisions through the sclera of the eye. Specifically, the engagement surface 812 of the illustrated embodiment has a generally spherical contour, complementary to the sclera of an eye. In other words, the engagement surface 812 defines a spherical surface, also indicated by the dotted line 1002, that is sized and shaped complementary to the sclera of an eye. The entry angle 1004 is generally equivalent to the angle between the trocar 136 and the normal or perpendicular line of the spherical surface 1002 defined by the engagement surface 812. The engagement member 806 and the engagement surface 812 are oriented relative to the rest of the surgical device 100 such that, when the engagement surface 812 is positioned flush with the sclera of the eye, the surgical device 100 is oriented at the predetermined entry angle 1004 relative to the point of incision of the trocar 136. In some embodiments, the predetermined entry angle 1004 is between 10° and 60°. In certain embodiments, the predetermined entry angle 1004 is between 20° and 50°, more suitably between 25° and 35°, and even more suitably, about 30°.

In some embodiments, such as the embodiment shown in FIG. 8, the engagement member 806 may be textured or include other gripping features to facilitate gripping the eye (or other organ or tissue) to maintain the position and orientation of the surgical device 100 relative to the eye. In the illustrated embodiment, the engagement member 806 includes laterally-spaced ridges 816 that protrude from the engagement surface 812. The ridges 816 facilitate gripping and reducing slippage between the eye and the engagement member 806 when the engagement surface 812 is positioned flush with the sclera of the eye.

In the illustrated embodiment, the engagement member 806 includes two alignment feet 810, and is symmetrical about the longitudinal axis 102 of the surgical device 100. Each of the alignment feet 810 includes an alignment edge 814 that is shaped complementary to the corneal limbus of the eye, and that has an arcuate shape that is convex with respect to the longitudinal axis 102 of the surgical device 100. The alignment feet 810 are laterally spaced from one another to permit the trocar-cannula assembly 114 to move axially past the alignment feet 810 when the propulsion system 116 is activated.

The configuration of the engagement member 806 and the alignment feet 810 allows the trocar-cannula assembly 114 to be inserted at a desired orientation (e.g., superiorly or temporally) without changing the entry angle of the trocar-cannula assembly 114. In particular, the positioning member 120 may be rotated 180° about the longitudinal axis 102 of the surgical device 100 to change the orientation at which the trocar-cannula assembly 114 is inserted (e.g., superiorly or temporally), without changing the resulting entry angle 1004 of the surgical device 100 relative to the eye. For example, for some surgical procedures, it is desirable for an instrument cannula (e.g., cannula 138) to point towards the surgeon, or away from the patient's nose. That is, it is desirable for the instrument cannula to point superiorly (i.e., with the proximal end of the cannula pointing towards the superior portion of the eye) when the cannula is inserted on the temporal or nasal side of the eye, and to point temporally (i.e., with the proximal end of the cannula pointing towards the temporal portion of the eye) when the cannula is inserted on the superior or inferior side of the eye. Accordingly, a surgeon may select which of the alignment feet 810 to use based upon the desired resulting orientation of the cannula 138 relative to the eye. For example, when forming an incision on the temporal side of an eye, aligning one of the alignment feet 810 with the corneal limbus will result in the trocar-cannula assembly 114 being oriented towards the inferior portion of the eye, while aligning the other of the alignment feet 810 with the corneal limbus will result in the trocar-cannula assembly 114 being oriented towards the superior portion of the eye. The trocar-cannula assembly 114 will be oriented at the same entry angle, regardless of which of the two alignment feet 810 is used.

In the illustrated embodiment, the positioning member 120 is formed separately from the handle 108, and connected to the handle 108 by inserting the connector portion 802 over the distal end of the handle 108 until the retention tabs 126 engage the distal surface of the connector portion 802. In other embodiments, the handle 108 and the positioning member 120 may be formed integrally as a single unit, for example, by injection molding or casting processes.

In use, the surgical device 100 is used to incise a tissue or organ and to insert the cannula 138 in the tissue or organ to provide access into a cavity. In ophthalmic surgical procedures, the surgical device 100 is used to form a sclerotomy at the Pars Plana within a patient's eye, and to insert the cannula 138 through the sclera of the eye to provide access to the posterior chamber of the eye.

In one embodiment, a method of using the surgical device 100 includes aligning the positioning member 120 with one or more anatomical features of the eye, such as the corneal limbus, pressing the engagement surface 812 flush against the sclera of the eye such that the surgical device 100 and the trocar-cannula assembly 114 are oriented at the desired predetermined entry angle 1004, and activating the propulsion system 116 using the activation device 150 to drive the trocar-cannula assembly 114 forward and form an incision through the sclera of the eye with the trocar 136.

In the example embodiment, aligning the positioning member 120 includes aligning at least one of the alignment feet 810 with an anatomical feature of the eye. Specifically, aligning the positioning member 120 includes aligning the alignment edge 814 of one of the alignment feet 810 with the corneal limbus of the eye. As noted above, aligning the alignment edge 814 with the corneal limbus provides a desired radial spacing between the limbus and the trocar insertion point, and facilities insertion of the trocar 136 through the Pars Plana.

When the propulsion system 116 is activated, the trocar-cannula assembly 114 is driven by the propulsion system 116 axially in the forward direction 118 by the stroke length 164. The propulsion system 116 stops forward advancement of the trocar-cannula assembly 114 just prior to the hub 502 of the cannula 138 contacting the sclera to prevent excess force being imparted to the sclera.

In the example embodiment, the propulsion system 116 is activated by depressing the trigger 152 until the latch 162 disengages the lip 708 of the piston 142. When the latch 162 disengages the lip 708 of the piston 142, the compressed helical spring 140 drives the piston 142 axially in the forward direction 118, and the piston 142 drives the trocar-cannula assembly 114 axially in the forward direction 118 by a distance equal to the stroke length 164. As the piston 142 is being driven forward, the trocar 136, followed by the shaft 504 of the cannula 138, enters the sclera via the Pars Plana at the predetermined entry angle 1004 determined by the positioning member 120. As noted above, the propulsion system 116 drives the trocar-cannula assembly 114 with a force and velocity greater than that typically applied by manual manipulation. In some embodiments, the propulsion system 116 moves the trocar-cannula assembly 114 by the stroke length 164 in less than about 0.5 seconds, or even less than about 0.1 seconds. The trocar 136 and cannula 138 are moving quickly enough that the inertia of the eye tissue is not overcome to a significant degree by the force generated during the creation of the incision and subsequent insertion of the cannula 138.

At the end of the piston stroke, the distal face of the cannula hub 502 is stopped just short of making contact with the sclera to prevent excess force being imparted to the sclera. In the illustrated embodiment, the stop pin 166 prevents forward axial travel of the piston 142 and the trocar-cannula assembly 114 beyond the stroke length 164 by engaging inner surfaces of the piston 142 along the elongate slot 714. Once the trocar 136 and cannula 138 have stopped, the surgeon removes the cannula 138 by sliding the cannula 138 along the trocar 136, and removing the trocar 136 from the surgical site.

In some embodiments, the surgical device 100 is a single use device, and is not intended to be reloaded or reused. In other embodiments, the surgical device 100 is configured for multiple uses, and may be sterilized and reloaded with another cannula after a first cannula is inserted into a surgical site. For example, after a first cannula is inserted into a surgical site, a second cannula may be inserted over the cutting tip 406 of the trocar 136, and moved axially along the trocar 136 to a desired position along the trocar 136. The propulsion system 116 may be "reloaded" by pushing the piston 142 axially backward into the cavity 130 of the handle 108 until the lip 708 of the piston 142 passes the latch 162 of the trigger 152. When the lip 708 of the piston 142 passes the latch 162, the trigger spring 154 moves the trigger 152 radial outward to the first, undepressed position (shown in FIG. 2), and the latch 162 engages the lip 708 of the piston 142, thereby inhibiting forward axial movement of the piston 142. In this state, the surgical device 100 is ready for use.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A surgical device comprising:
    a trocar;
    a cannula releasably mounted on the trocar, the cannula including a hub and having a central opening through which the trocar extends;
    a propulsion system operatively connected to the trocar and operable to drive the trocar axially in a forward direction away from a proximal end of the surgical device; and
    a positioning member disposed at a distal end of the surgical device, the positioning member including a leg extending distally from a proximal portion of the positioning member and an engagement member disposed at a distal end of the leg, the engagement member having a contoured, distal-facing engagement surface that, when engaged with an eye of a patient, causes the trocar to be oriented relative to the eye at a predetermined oblique entry angle,
    wherein the leg extends only partially around a longitudinal axis of the surgical device to define a viewing window that provides direct line-of-sight to an incision site; and
    wherein the engagement member includes two alignment feet laterally spaced apart from one another, each alignment foot having a lateral outer surface that adjoins the engagement surface at an alignment edge defining an outer boundary of the engagement surface, wherein each alignment edge defines an arcuate shape having a radius of curvature that is complementary to a corneal limbus of the eye such that the trocar can be oriented at the predetermined oblique entry angle when either of the alignment feet is aligned with the corneal limbus of the eye.

2. The surgical device of claim 1 further comprising an activation device operatively connected to the propulsion system and operable to activate the propulsion system in response to a user input.

3. The surgical device of claim 2, wherein the activation device includes a trigger extending radially outward from a handle of the surgical device.

4. The surgical device of claim 1, wherein the cannula includes a valve operable to inhibit fluid flow through the central opening.

5. The surgical device of claim 4, wherein the valve includes at least one valve member biased against the trocar to maintain a position of the cannula relative to the trocar.

6. The surgical device of claim 1, wherein the trocar has an outer diameter less than or equal to 23-gauge.

7. The surgical device of claim 1, wherein the propulsion system is configured to displace the trocar by a stroke length from an initial position to a second, fully extended position in less than 0.5 seconds.

8. The surgical device of claim 1, wherein the propulsion system is configured to drive the trocar at a velocity of between 0.05 meters per second (m/s) and 1 m/s.

9. The surgical device of claim 1, wherein the propulsion system is configured to drive the trocar at a velocity of between 0.1 m/s and 1 m/s.

10. The surgical device of claim 1, wherein the positioning member is configured to orient the trocar at an entry angle of between 10° and 60° when the engagement surface is engaged with the eye of the patient.

11. The surgical device of claim 1, wherein the propulsion system is operable to displace the trocar by a stroke length and stop continued forward movement of the trocar following displacement of the trocar by the stroke length to prevent the hub of the cannula from moving axially past the engagement surface.

12. A method of using a surgical device to insert a trocar-cannula assembly into eye tissue, the trocar-cannula assembly including a trocar and a cannula releasably mounted on the trocar, the cannula including a hub and having a central opening through which the trocar extends, the surgical device including a propulsion system operatively connected to the trocar-cannula assembly, and a positioning member disposed at a distal end of the surgical device, the positioning member including a leg extending distally from a proximal portion of the positioning member and an engagement member disposed at a distal end of the leg, the engagement member having a contoured, distal-facing engagement surface and two alignment feet laterally spaced apart from one another, each alignment foot having a lateral outer surface that adjoins the engagement surface at an alignment edge defining an outer boundary of the engagement surface, the leg extending only partially around a longitudinal axis of the surgical device to define a viewing window that provides direct line-of-sight to an incision site, the method comprising:
    engaging the eye tissue with the contoured engagement surface, wherein engaging the eye tissue with the contoured engagement surface causes the trocar-cannula assembly to be oriented at a predetermined oblique entry angle relative to the eye tissue, wherein each alignment edge defines an arcuate shape having a radius of curvature that is complementary to a corneal limbus of the eye such that the trocar can be oriented at the predetermined oblique entry angle when either of the alignment feet is aligned with the corneal limbus of the eye;
    activating the propulsion system; and
    driving the trocar-cannula assembly with the propulsion system axially in a forward direction away from a proximal end of the surgical device and into the eye tissue at the predetermined oblique entry angle.

13. The method of claim 12, further comprising aligning a portion of the positioning member with the corneal limbus of the eye.

14. The method of claim 12, further comprising stopping the trocar-cannula assembly prior to the hub of the cannula contacting the eye tissue.

15. The method of claim 12, wherein the predetermined entry angle is between 10° and 60°, and wherein engaging the eye tissue with the contoured engagement surface causes the trocar-cannula assembly to be oriented at an entry angle of between 10° and 60°.

16. The method of claim 12, wherein the propulsion system is operable to axially displace the trocar-cannula assembly by a stroke length, and wherein driving the trocar-cannula assembly includes axially displacing the trocar-cannula assembly by the stroke length in less than 0.5 seconds.

17. The method of claim 16, wherein driving the trocar-cannula assembly includes axially displacing the trocar-cannula assembly by the stroke length in less than 0.1 seconds.

18. The method of claim 12, wherein driving the trocar-cannula assembly includes driving the trocar-cannula assembly at a velocity of between 0.05 m/s and 1 m/s.

19. The method of claim 12, wherein driving the trocar-cannula assembly includes driving the trocar-cannula assembly at a velocity of between 0.1 m/s and 1 m/s.

\* \* \* \* \*